US012688577B2

(12) United States Patent
Sousa Ferreira et al.

(10) Patent No.: US 12,688,577 B2
(45) Date of Patent: Jul. 21, 2026

(54) AUTOMATIC DETECTION AND DIFFERENTIATION OF SMALL BOWEL LESIONS IN CAPSULE ENDOSCOPY

(71) Applicant: DIGESTAID—ARTIFICIAL INTELLIGENCE DEVELOPMENT, LDA, Gondomar (PT)

(72) Inventors: João Pedro Sousa Ferreira, Oporto (PT); Miguel José Da Quinta E Costa De Mascarenhas Saraiva, Oporto (PT); Hélder Manuel Casal Cardoso, Valbom Gondomar (PT); Manuel Guilherme Goncalves De Macedo, Oporto (PT); João Pedro Lima Afonso, Mazedo Moncao (PT); Ana Patricia Ribeiro Andrade, Oporto (PT); Renato Manuel Natal Jorge, Oporto (PT); Marco Paulo Lages Parente, Oporto (PT)

(73) Assignee: Digestaid—Artificial Intelligence Development, LDA, Gondomar (PT)

( * ) Notice: Subject to any disclaimer, the term of this patent is extended or adjusted under 35 U.S.C. 154(b) by 454 days.

(21) Appl. No.: 18/037,963

(22) PCT Filed: Nov. 18, 2021

(86) PCT No.: PCT/PT2021/050039
§ 371 (c)(1),
(2) Date: May 19, 2023

(87) PCT Pub. No.: WO2022/108464
PCT Pub. Date: May 27, 2022

(65) Prior Publication Data
US 2024/0013377 A1 Jan. 11, 2024

(30) Foreign Application Priority Data

Nov. 19, 2020 (PT) ........................................ 116894

(51) Int. Cl.
*G06T 7/00* (2017.01)
*A61B 1/04* (2006.01)

(52) U.S. Cl.
CPC ............ *G06T 7/0012* (2013.01); *A61B 1/041* (2013.01); *G06T 2207/10068* (2013.01);
(Continued)

(58) Field of Classification Search
CPC ......... G06T 7/0012; G06T 2207/10068; G06T 2207/20081; G06T 2207/20084;
(Continued)

(56) References Cited

U.S. PATENT DOCUMENTS

2018/0247107 A1* 8/2018 Murthy ............... G06V 20/698
2020/0279373 A1* 9/2020 Hussain ................ G16H 50/70
(Continued)

OTHER PUBLICATIONS

Patent Cooperation Treaty, Written Opinion and International Search Report issued in PCT/PT2021/050039, Mar. 10, 2022, pp. 1-16.
(Continued)

*Primary Examiner* — Van D Huynh
(74) *Attorney, Agent, or Firm* — Heisler & Associates

(57) ABSTRACT

The present invention relates to a computer-implemented method capable to automatically characterize small bowel lesions in capsule endoscopy images, comprising detecting small bowel lesions in medical images by classifying pixels
(Continued)

as lesion or non-lesion, using a convolutional image feature extraction step followed by an architecture of classification and indexing into one or more classes.

11 Claims, 12 Drawing Sheets

(52) U.S. Cl.
CPC .............. *G06T 2207/20081* (2013.01); *G06T 2207/20084* (2013.01); *G06T 2207/30028* (2013.01); *G06T 2207/30096* (2013.01)

(58) Field of Classification Search
CPC . G06T 2207/30028; G06T 2207/30096; A61B 1/041; A61B 5/6861; G06N 3/0464; G06N 3/0895; G06N 3/09; G06N 3/096; G06N 3/0985; G06N 3/045; G06V 10/82; G06V 2201/031; G06F 18/00
See application file for complete search history.

(56) References Cited

U.S. PATENT DOCUMENTS

| | | | | |
|---|---|---|---|---|
| 2021/0153808 A1* | 5/2021 | Tada | ....................... | A61B 6/032 |
| 2021/0398676 A1* | 12/2021 | Evans | .................... | G16H 30/40 |
| 2022/0020496 A1* | 1/2022 | Saito | ..................... | G06T 7/0012 |
| 2022/0031227 A1* | 2/2022 | Cho | ..................... | A61B 1/2736 |
| 2023/0148834 A1* | 5/2023 | Baras | ........................ | G06T 7/11 |
| | | | | 382/128 |
| 2023/0215570 A1* | 7/2023 | Ji | ........................... | C12Q 1/045 |
| | | | | 702/19 |
| 2023/0298306 A1* | 9/2023 | Baras | ..................... | G06F 18/22 |
| | | | | 382/128 |

OTHER PUBLICATIONS

Valerio et al., "Lesions Multiclass Classification in Endoscopic Capsule Frames", Procedia Computer Science, 2019, pp. 637-645, vol. 164.

Wang et al., "A systematic evaluation and optimization of automatic detection of ulcers in wireless capsule endoscopy on a large dataset using deep convolutional neural networks", Physics in Medicine and Biology, Institute of Physics Publishing, Dec. 5, 2019, pp. 1-13, vol. 64(23).

Yan et al., "Intelligent diagnosis of gastric intestinal metaplasia based on convolutional neural network and limited number of endoscopic images", Computers in Biology and Medicine, Oct. 12, 2020, pp. 1-8, vol. 126.

Kyriakides et al., "An Introduction to Neural Architecture Search for Convolutional Networks", arxiv.org, University of Macedonia, May 22, 2020, pp. 1-17.

* cited by examiner

| Evaluation of method 9000 | Best overall accuracy (mean ± standard deviation in %) | |
| --- | --- | --- |
| | with method 8000 (our method) | without method 8000 |
| VGG | 82.3 ± 2.1 | 79.7 |
| ResNet50 | 81.1 ± 3.5 | 77.8 |
| ResNet125 | 84.2 ± 4.6 | 79.7 |
| InceptionV3 | 89.8 ± 5.1 | 84.6 |
| MobileNet | 65.9 ± 1.7 | 64.5 |
| Xception | 93.7 ± 4.4 | 89.3 |
| EfficientNetB3 | 88.3 ± 3.7 | 85.9 |
| EfficientNetB5 | 90.2 ± 4.1 | 87.4 |
| EfficientNetB7 | 94.4 ± 5.6 | 90.4 |

FIG. 11

AUTOMATIC DETECTION AND DIFFERENTIATION OF SMALL BOWEL LESIONS IN CAPSULE ENDOSCOPY

RELATED PATENT APPLICATIONS

This patent application is the National Phase of International Application No. PCT/PT2021/050039, filed Nov. 18, 2021, which designated the U.S. and that International Application was published under PCT Article 21(2) in English, which claims the benefit of priority to Portuguese Patent Application No. 116894, filed Nov. 19, 2020. The entire contents of the foregoing applications are incorporated herein by reference, including all text, tables and drawings.

BACKGROUND OF THE INVENTION

The present invention relates to the lesion detection and classification in medical image data. More particularly, to automated identification of small bowel lesions in capsule endoscopy images to assess the lesion seriousness and subsequent medical treatment.

Capsule endoscopy has become the primary endoscopic modality for small bowel exams. By carefully examining the video frames of the capsule, physicians are able to detect, identify and characterize lesions in the inner walls of the gastrointestinal tract. Such examination of video capsule endoscopies is, however, significantly time-consuming for gastroenterologists and prone to human error and oversight. Conversely, in capsule endoscopy, the record of such images is readily available and digitally stored for posterior review and comparison. Within this context, image data creates a robust ground for computer-aided diagnosis using machine learning systems for lesion characterization and, consequently, decision making. The goal of the lesion detection and classification of small bowel lesions is to yield a more accurate, thoroughly automated characterization of the lesion seriousness and aid in the medical diagnosis and treatment.

Valerio, Maria Teresa, et al. in "Lesions Multiclass Classification in Endoscopic Capsule Frames." Procedia Computer Science 164 (2019): 637-645 raised awareness for the time-consuming and error-prone identification of small bowel lesions by medical experts. Furthermore, the authors proposed an automatic approach for identifying these lesions based on deep learning networks on medically annotated wireless capsule endoscopy images.

Li, Xiuli, et al. in "Exploring transfer learning for gastrointestinal bleeding detection on small-size imbalanced endoscopy images." 2017 39th Annual International Conference of the IEEE Engineering in Medicine and Biology Society (EMBC). IEEE, 2017 explored transfer learning for gastrointestinal bleeding detection on a small-size cohort of endoscopy images with the usage of neural networks on large-scale image representations.

Document CN 110705440 filters the image into three channels and separately inputs them in a convolutional network model, trained with the Kvasir dataset.

Document US 2020/065961 A1 uses a convolutional network to classify data in different granulation scales to detect lesions in biological tissue. The data requires the identification in the image of the defect/injury zone.

Document CN 111127412A provides a pathological image recognition device based on a generation countermeasure network, aiming at solving the problems of dependence on experience, time-consuming manual labelling cost, low recognition efficiency and poor accuracy of the existing other pathological recognition methods. The method is evaluated for Crohn's disease lesions but does not distinguish which type of lesion each image presents.

Document CN 107730489A discloses a wireless capsule endoscope with a small intestine lesion meter to efficiently and accurately detect small bowel lesions. The classification and positioning of small intestine lesions are achieved by an image segmentation algorithm. The document does not use transfer learning, does not differentiate lesion types nor does it actively update training data with the new data for the next training generation.

Document CN 111739007A discloses a bubble area identifier trained by a convolutional neural network which doesn't consider the classification of small bowel lesions.

Gastrointestinal diseases, such as internal lesions in the small bowel, are epidemiologically common diseases. Often, when not diagnosed and treated these lesions, may have an unfavorable clinical outcome. Gastrointestinal endoscopy has a pivotal role in diagnosing and treating digestive cancer, inflammatory bowel disease, and other gastrointestinal pathologies. For example, if detected early, the colorectal polyp can be safely removed and prevent colorectal cancer. Hence, it is imperative to detect all polyps. Another example of the critical role of gastrointestinal endoscopy is the endoscopic evaluation of inflammatory bowel activity by detecting ulcers and erosions in the small bowel and colon. Evaluating inflammatory bowel activity is crucial for diagnosing, treating, and managing patients with inflammatory bowel disease. However, gastrointestinal endoscopy is a time and resource-consuming, and challenging task. Occasionally, the endoscopist may present signs of fatigue or suffer from an attention deficit, failing to identify all the relevant endoscopic findings accurately. More specifically, capsule endoscopy is a minimally invasive alternative for evaluating the gastrointestinal tract, particularly for the small bowel endoscopic examination. Indeed, capsule endoscopy is the gold standard and first-line exam for evaluating the small bowel, namely in obscure gastrointestinal bleeding and small bowel pathologies.

Endoscopic image acquisitions are the state-of-the-art technique for an insight into the patients' intestinal tract. Usually the endoscopic elements are provided with a portable image recording device and means to convert these captures to a digitized representation and capable of being stored in a personal computer.

Endoscopic images, due to the nature of their acquisition, often lack the light or other photographic conditions to allow the classification of small bowels straightforwardly executed. Within this context, machine learning techniques have been presented to automatically execute such task but up-to-date they have failed to present overall accuracy or false-negative rate that can be used in clinical practice and hence leads to inappropriate treatment.

BRIEF SUMMARY OF THE INVENTION

The present invention provides a method for deep learning based identification of prevalent lesions of the small bowel in endoscopic images and accurately differentiate them. Such automatic identification, classification and hemorrhagic risk estimation of small bowel lesions are used in clinical practice for diagnosis and treatment planning.

Initially, by using pre-trained convolutional layers of a given architecture with the ImageNet[1] set and further testing them using a subset of endoscopy images per capsule the potential to detect injuries is shown. The clinical disruptive nature of the present invention is supported by the artificial intelligence system ability to not only detect but also accurately differentiate all the relevant endoscopic findings/ lesions. Indeed, the capacity of the neural network to differentiate lesions of subtle pleomorphic nature is of the outmost importance in clinical practice, allowing a complete capsule endoscopy diagnosis.

Furthermore, the stratification of the hemorrhagic potential of each lesion is a relevant novelty introduced by this invention to the current state of the art. One of the most important and frequent indication for performing capsule endoscopy is obscure gastrointestinal bleeding, and the correct assessment of the hemorrhagic potential of the endoscopic findings is critical for the clinical follow up management. Therefore, the present invention, by accurately predicting the hemorrhagic potential of capsule endoscopy findings/lesions, helps the clinical team to better define the diagnostic and therapeutic management of the patient, which may translate into optimized clinical outcomes.

This technology can be applied in capsule endoscopy software in order to help the gastroenterologist in the detection of small bowel lesions. Furthermore, capsule endoscopy is an expensive exam, with increasing relevance and application in clinical practice.

The following were considered relevant to highlight the problem solved by the present invention from the methods known in the art to detect and differentiate small intestine lesions in capsule endoscopy.

Preferred is a method where machine learning techniques are used to classify an image. Deep learning uses algorithms to model high-level abstractions in data using a deep graph with multiple processing. Using a multilayered architecture, machines employing deep learning techniques process raw data to find groups of highly correlated values or distinctive themes.

The method detects relevant small bowel lesions in capsule endoscopy images and differentiates according to their bleeding potential using the Saurin's classification system. Saurin's classification system measures the bleeding potential of a small bowel lesion. It is a useful tool for the evaluation and treatment strategy of patients. Its usage has a direct impact on clinician diagnosis and decision-making. Such embodiment of the present invention uses transfer learning and semi-active learning. Transfer learning allows feature extraction and high-accuracy classification using reasonable datasets sizes. Semi-active implementation allows a continuous improvement in the classification system. The preferred embodiment of the present invention preferably can use transfer learning for feature extraction on capsule endoscopy images according to the Saurin's classification system or semi-active learning strategy for capsule endoscopy images.

Subsequently the method splits the dataset into a number of stratified folds, preferably where images relative to a given patient are included in one fold only. Further, additionally or alternatively, such data are trained and validated with patient grouping to a random fold, i.e., images from an arbitrary patient belong to either the training or the validation set.

Preferred is a method which uses the chosen training and validation sets to further train a series of network architectures combinations, which include, among others, a feature extraction, and a classification component. The series of convolutional neural networks to train include but is not limited to: VGG16, InceptionV3, Xception EfficientNetB5, EfficientNetB7, Resnet50, and Resnet125. Preferably, their weights are frozen, with exception to the BatchNormalization layers, and are coupled with a classification component. The classification component comprises at least two dense layers, preferably of sizes 2048 and 1024, and at least one dropout layer of preferably in between them.

Alternatively, but not preferentially, the classification component can be used with more dense layers or with dense layers of different size. Alternatively, but not preferentially, the classification component can also be used without dropout layers.

Further, additionally, the best performing architecture is chosen according to the overall accuracy and sensitivity. Performance metrics include but are not limited to f1-metrics. Further, the method preferably uses the best performing architecture for training a series of classification component combinations which preferably include but are not limited to two to four dense layers in sequence, starting with 4096 and decreasing in half up to 512. Between the final two layers there is a dropout layer of 0.1 drop rate.

Lastly, the best performing solution is trained using the whole dataset with patient grouping.

Further embodiments of the present invention may include similar classification networks, training weights and hyperparameters.

These may include the usage of any image classification network, new or not yet designed.

In general, the method includes two modules that provided the required data for the remaining: prediction and output collector. Prediction collector reads videos and selects images with findings. The output collector passes these images with findings for processing.

Examples of advantageous effects of the present invention include: training using parameters from machine learning results of cloud-based every-day increasing datasets; automatically prediction of the endoscopy image by using a deep learning method so that the small bowel lesions from image input of the capsule endoscope can be identified and differentiated according to the Saurin's classification system; the usage of transfer learning improves the image classification speed and corresponding classification accuracy.

BRIEF DESCRIPTION OF THE DRAWINGS

Figure 6:
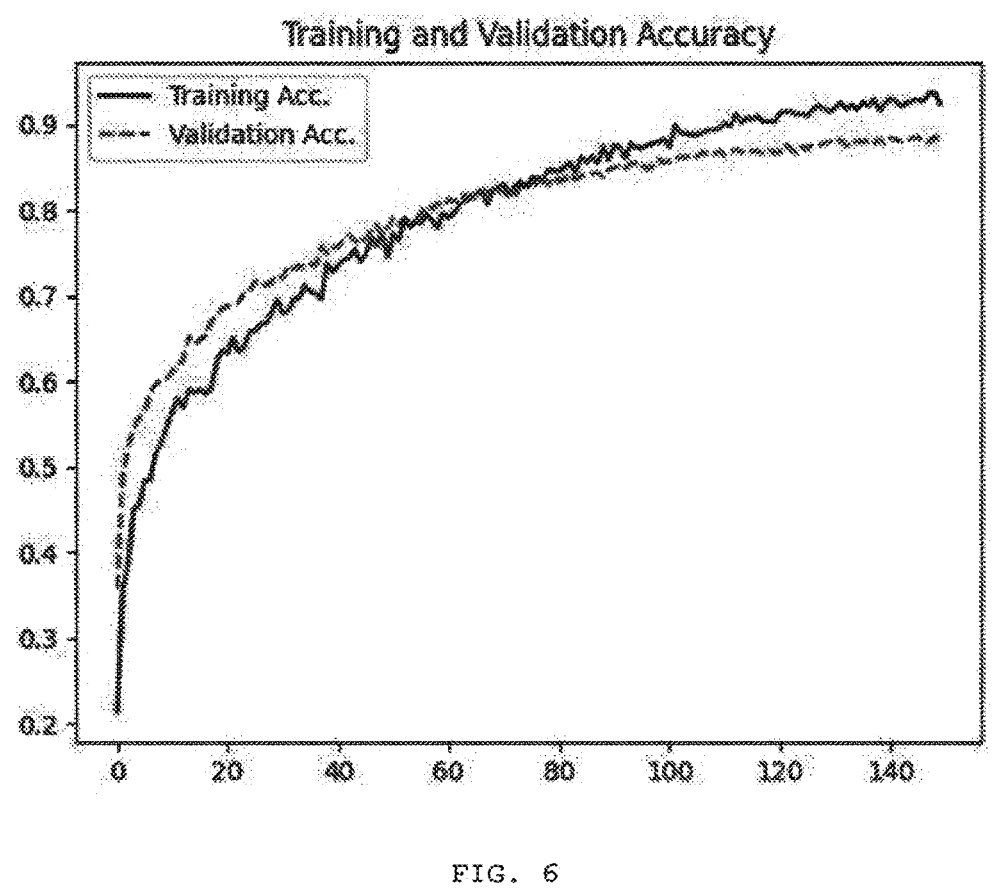

FIG. 6 illustrates a preferable embodiment of the present invention where the accuracy curves for the training on a small subset of images and labelled data are shown. Example of results from an iteration of method 8000.

FIG. 7 illustrates exemplary accuracy curves during training on a small subset of images and labelled data and according to an embodiment of the present invention. Example of results from an iteration of method 8000.

FIG. 11 illustrates a result of performing deep learning-based lesion classification on the data volume 240 and 250, according to an embodiment of the present invention.

DETAILED DESCRIPTION

Figure 1:
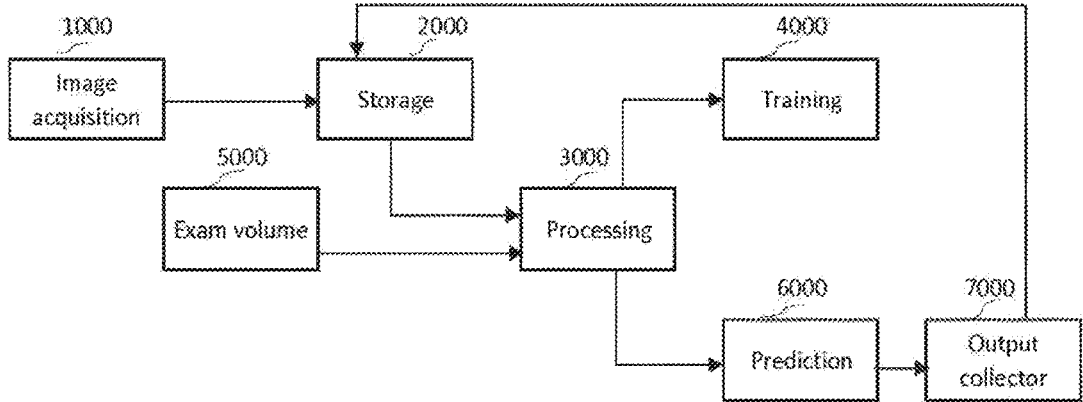
FIG. 1 illustrates a method for small bowel lesion classification in capsule endoscopy according to an embodiment of the present invention.

The present invention discloses a new method and system capable of detecting and differentiating lesions in images acquired during a capsule endoscopy exam.

Some preferable embodiments will be described in more detail with reference to the accompanying drawings, in which the embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

The term "deep learning" is a machine learning technique that uses multiple data processing layers to classify the data sets with high accuracy. It can be a training network (model or device) that learns based on a plurality of inputs and outputs. A deep learning network can be a deployed network (model or device) generated from the training network and provides an output response to an input.

The term "supervised learning" is a deep learning training method in which the machine is provided already classified data from human sources. In supervised learning, features are learned via labeled input.

The term "convolutional neural networks" or "CNNs" are networks that interconnect data used in deep learning to recognize objects and regions in datasets. CNNs evaluate raw data in a series of stages to assess learned features.

The term "transfer learning" is a machine storing the information learned when attempting to solve one problem to solve another problem of similar nature as the first.

We use the term "semi-active learning" as a process of machine learning. Before executing the next learning process, the training network appends a set of labeled data to the training dataset from a trusted external entity. For example, as a machine collects more samples from specialized staff steps, the less prone it is to mispredict images of identical characteristics.

The term "computer-aided diagnosis" refers to machines that analyze medical images to suggest a possible diagnosis.

The term "Lymphangiectasia" represent obstructed and dilated lymphatic capillaries. It may be functional (without association to pathology), primary or secondary to other conditions. We defined lymphangiectasia according to previously published material as scattered whitish spots of the intestinal mucosa. These mucosal alterations may be diffuse or patchy.

The term "xanthomas" result from the accumulation of cholesterol-rich material in enteric mucosal macrophages. The endoscopic finding in capsule endoscopy was defined as plaque-like lesions with whitish/yellowish appearance.

The terms "ulcers" and "erosions" represent mucosal breaks in the mucosa of the small bowel. These lesions are distinguished based on estimated size and depth of penetration. "Ulcers" were defined as a depressed loss of epithelial covering, with a whitish base and surrounding swollen mucosa with >5 mm of diameter. Conversely, mucosal "erosions" were defined as a minimal loss of epithelial layering surrounded by normal mucosa.

The term "vascular lesions" of the small bowel include a large variety of individual lesions, specifically red spots, angiectasia, varices and phlebectasia. Red spots were defined as punctuate (<1 mm) flat lesion with a bright red area, within the mucosal layer, without vessel appearance. Angiectasia were defined as well demarcated bright red lesions consisting of tortuous and clustered capillary dilatations, within the mucosal layer. Varices were defined as raised venous dilatation with serpiginous appearance. Phlebectasia were identified if a regular bluish venous dilatation running below the mucosa was detected.

The term "Protruding lesions" encompass lesions bulging towards the lumen of the small bowel. These lesions may have distinct etiologies and include polyps, epithelial tumors, subepithelial lesions and nodules.

The term "Blood" is used to represent the presence of bright blood occupying part or the total section of the enteric lumen. It represents active or recent bleeding. "Hematic residues" represent fragmented or entire blood clots seen as dark red or brown residues in the lumen of the small bowel or adherent to the mucosa. Isolated these residues represent previous bleeding.

The present invention relates to a method for deep learning based small bowel lesion classification in capsule endoscopy images, according to their bleeding potential (FIG. 1). Often, embodiments of the present invention provide a visual understanding of the deep learning small bowel lesion classification method. Automatic lesion classification of small bowel images in capsule endoscopy is a challenging task since lesions with different bleeding potential have similar shape and contrast. Large variations in the small bowel preparation before capsule ingestion further complicates automated small bowel lesion classification. Although the automatic training and classification times are fast (on average 10 seconds for a test dataset of 2000 images), the output is not satisfactory for a fast diagnosis by the experts.

The method comprises an image acquisition module; a storage module; a training input module; a processing module; an exam input module; a training module; a prediction module; an output collector module.

Figure 4:
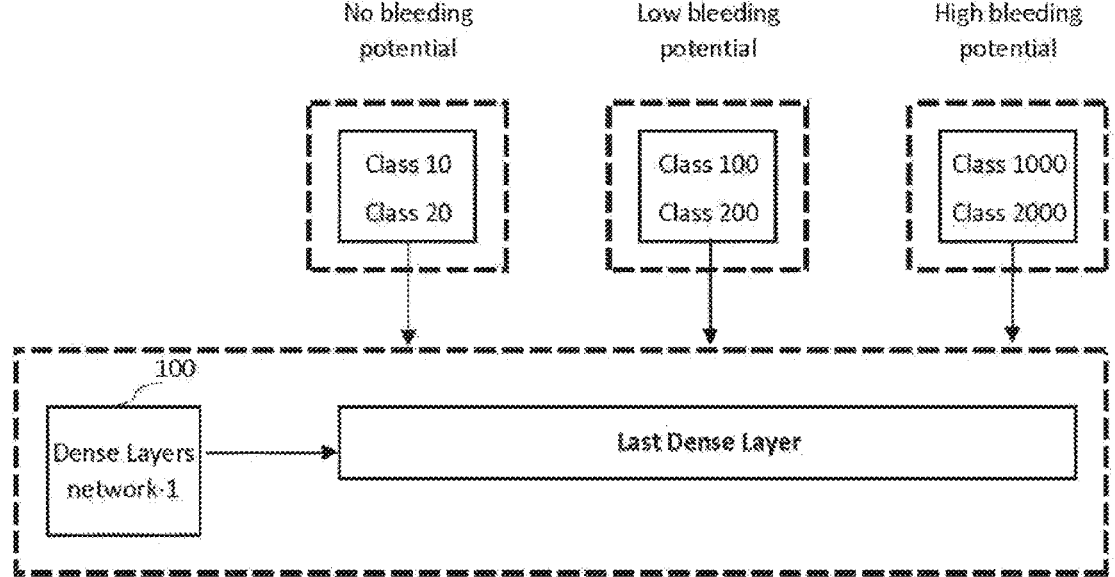
FIG. 4 illustrates the structure of the classification network to distinguish according to bleeding potential.

The image acquisition module 1000 receives exam input volumes from capsule endoscopy providers. Merely as exemplificative, the providers can be, but not only, OMOM, Given, Mirocam, and Fujifilm. Images 1000 and corresponding labels are loaded onto the storage module 2000. The storage module 2000 includes a multitude of classification network architectures 100, trained convolutional network architectures 110 and hyperparameters for from training. The storage module 2000 can be a local or cloud server. The storage module contains training input labelled data from capsule endoscopy images and the required metadata to run processing module 3000, training module 4000, prediction module 5000, a second prediction module 6000, and output collector module 7000. The input labelled data includes, but not only, images and corresponding lesion classification. The metadata includes, but not only, a multitude of classification networks architectures 100 exemplified in FIG. 4, a multitude of trained convolutional neural networks architectures 110, training hyperparameters, training metrics, fully trained models, and selected fully trained models.

Images and labelled data at the storage module 2000 are processed at the processing module 3000 before running the optimized training at the training module 4000. The processing module normalizes the images according to the deep model architecture, to be trained at 3000 or evaluated at 4000. By manual or scheduled request, the processing module normalizes the image data at the storage module 2000 according to the deep model architectures that will run at training module 4000. Optionally by manual or scheduled request, the processing module generates the data pointers to the storage module 2000 to form the partial or full images and ground-truth labels required to run the training module 3000. To prepare each training session, a dataset is divided into folds, where patient-specific imagery is exclusive to one and one fold only, for training and testing. The training set is split for model training to generate the data pointers of the all images and ground-truth labels, required to run the training process 9000. k-fold is optionally applied with stratified grouping by patient in the training set to generate the data pointers of the partial images and ground-truth labels, required to run the model verification process 8000 of the training module 4000. The split ratios and number of folds are available at the metadata of the storage module. Operators include but are not limited to users, a convolutional neural network trained to optimize the k-fold or a mere computational routine adapted to perform the task. Merely as an example, the dataset is divided with patient split into 90% for training and 10% for testing. Optionally, images selected for training can be split into 80% for training and 20% for validation during training. A 5-fold with stratified grouping by patient is applied in the images selected for training. By manual or scheduled request, the processing module normalizes the exam volume data 5000 according to the deep model architecture to run at the prediction module 6000.

Figure 2:
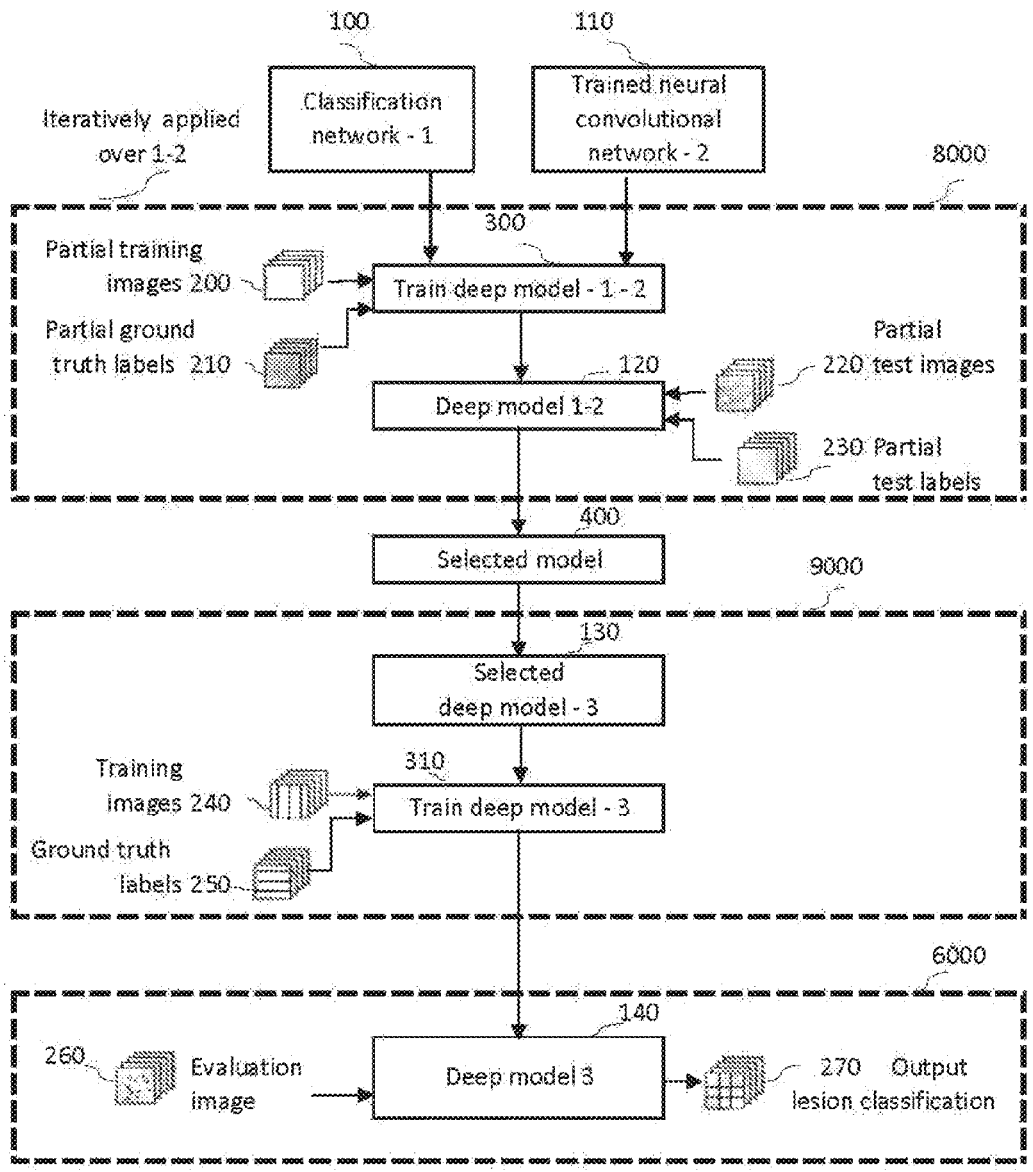
FIG. 2 illustrates the method for automatic detection and differentiation of small bowel lesions in capsule endoscopy exam.
Figure 3:
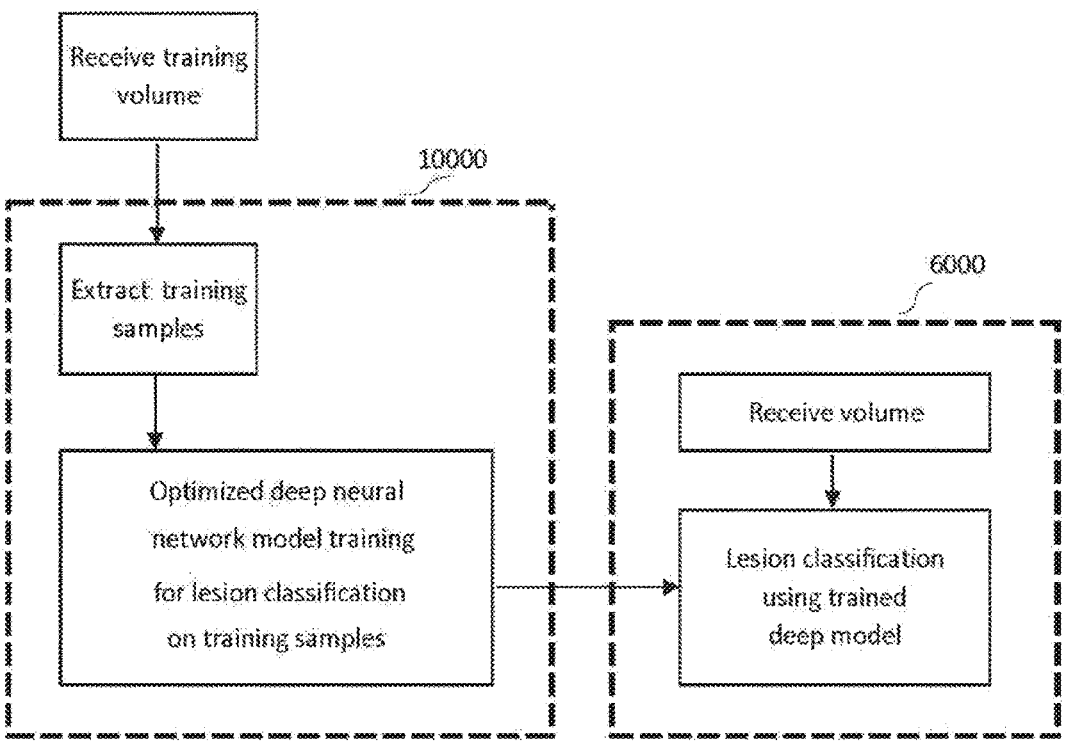
FIG. 3 illustrates the major processes for automatic detection and differentiation of small bowel lesions in capsule endoscopy exam.

As seen in FIG. 2, the training module 4000 has a model verification process 8000, a model selection step 400 and a model training step 9000. The model verification part iteratively selects combinations of classification architectures 100 and convolutional networks 110 to train a deep model for small bowel lesion classification. The classification network 100 has Dense and Dropout layers to classify small bowel lesions according to their hemorrhagic potential. A neural convolutional network 110 trained on large datasets is coupled to the said classification network 100 to train a deep model 300. Partial training images 200 and ground-truth labels 210 train the said deep model 300. The performance metrics of the trained deep model 120 are calculated using a plurality of partial training images 220 and ground-truth labels 230. The model selection step 400 is based on the calculated performance metrics. The model training part 9000 trains the selected deep model architecture 130, at process 310, using the entire data of training images 240 and ground-truth labels 250. At the prediction module 6000, the trained deep model 140 outputs small bowel lesion classification 270 from a given evaluation image 260. An exam volume of data 5000 comprising the images from the capsule endoscopy video is the input of the prediction module 6000. The prediction module 6000 classifies image volumes of the exam volume 5000 using the best-performed trained deep model from 4000 (see FIG. 3). An output collector module 7000 receives the classified volumes and load them to the storage module after validation performed by a neural network or any other computational system adapted to perform the validation task or optionally a physician expert in gastroenterological imagery.

Embodiments of the present invention provide a deep learning-based method for automatic lesion classification of small bowel images in capsule endoscopy. Such methods described herein achieve improved recognition quality and diagnosis usefulness when compared with the existing computer-based methods described above for lesion classification capsule endoscopy image. The existing methods for small bowel lesion classification do not use transfer learning neither semi-active training. This improved classification model results from an optimized training pipeline on a multitude of deep model architectures.

Merely as exemplificative, the invention comprises a server containing training results for architectures in which training results from large cloud-based large datasets such as, but not only, ImageNet, ILSVRC, and JFT are available. The architecture variants include, but not only, VGG, ResNet, Inception, Xception or Mobile, EfficientNets, among others. All data and metadata can be stored in a cloud-based solution or on a local computer. Embodiments of the present invention also provide various approaches to make a faster deep model selection. FIG. 2 illustrates a method for deep learning small bowel lesion classification according to an embodiment of the present invention. The method of FIG. 2 includes a pretraining stage 8000, a training stage 9000. The training stage 8000 is performed with early stopping on small subsets of data to select the best-performed deep neural network for small bowel lesion classification among multiple combinations of convolution and classification parts. For example, a classification network of two dense layers of size 512 is coupled with the Xception model to train on a random set resulting from k-fold cross validation with patient grouping. Another random set is selected as the test set.

The process of training 8000 with early stopping and testing on random subsets is repeated in an optimization loop for combinations of (i) classification and transfer-learned deep neural networks; (ii) training hyperparameters. The image feature extraction component of the deep neural network is any architecture variant without the top layers accessible from the storage module. The layers of the feature extraction component remain frozen but are accessible at the time of training via the mentioned storage module. The BatchNormalization layers of the feature extraction component are unfrozen, so the system efficiently trains with capsule endoscope imagens presenting distinct features from the cloud images. The classification component has at least two blocks, each having, among others, a Dense layer followed by a Dropout layer. The final block of the classification component has a BatchNormalization layer followed by a Dense layer with the depth size equal to the number of lesions type one wants to classify.

The fitness of the optimization procedure is computed to (i) guarantee a minimum accuracy and sensitivity at all classes, defined by a threshold (ii) minimize differences between training, validation, and test losses; (iii) maximize learning on the last convolutional layer. For example, if a training shows evidence of overfitting, a combination of a less deep model is selected for evaluation.

The training stage 9000 is applied on the best performed deep neural network using the whole dataset.

The fully trained deep model 140 can be deployed onto the prediction module 6000. Each evaluation image 260 is then classified to output a lesion classification 270. The output collect module has means of communication to other systems to perform expert validation and confirmation on newly predict data volumes reaching 270. Such means of communication include a display module for user input, a thoroughly trained neural network for decision making or any computational programmable process to execute such task. Validated classifications are loaded on the storage module to become part of the datasets needed to run the pipelines 8000 and 9000, either by manual or schedule requests.

Figure 5:
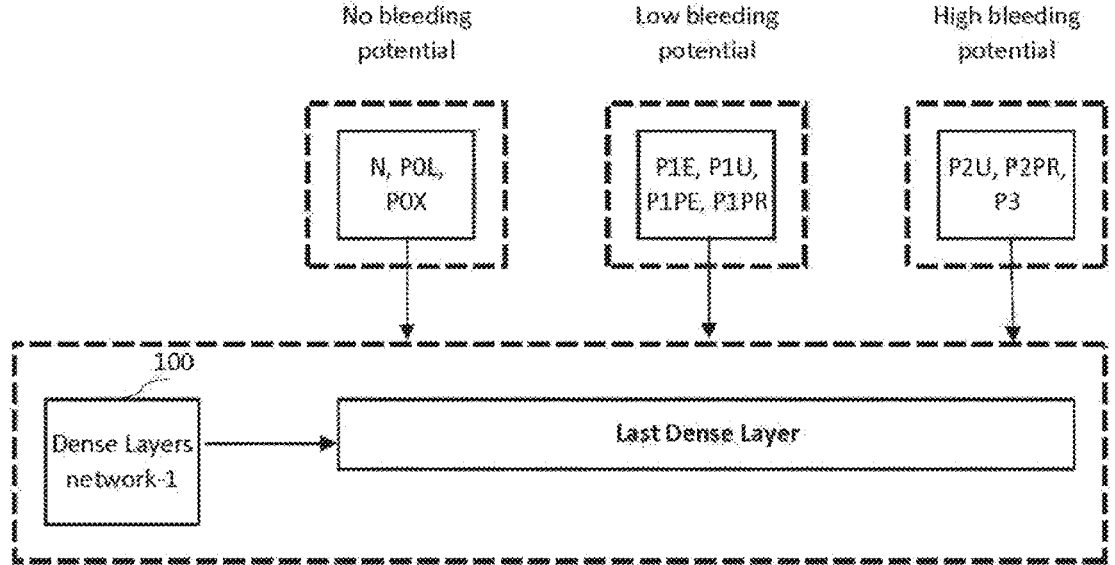
FIG. 5 depicts an embodiment of the classification network to classify according to bleeding potential.
Figure 7:
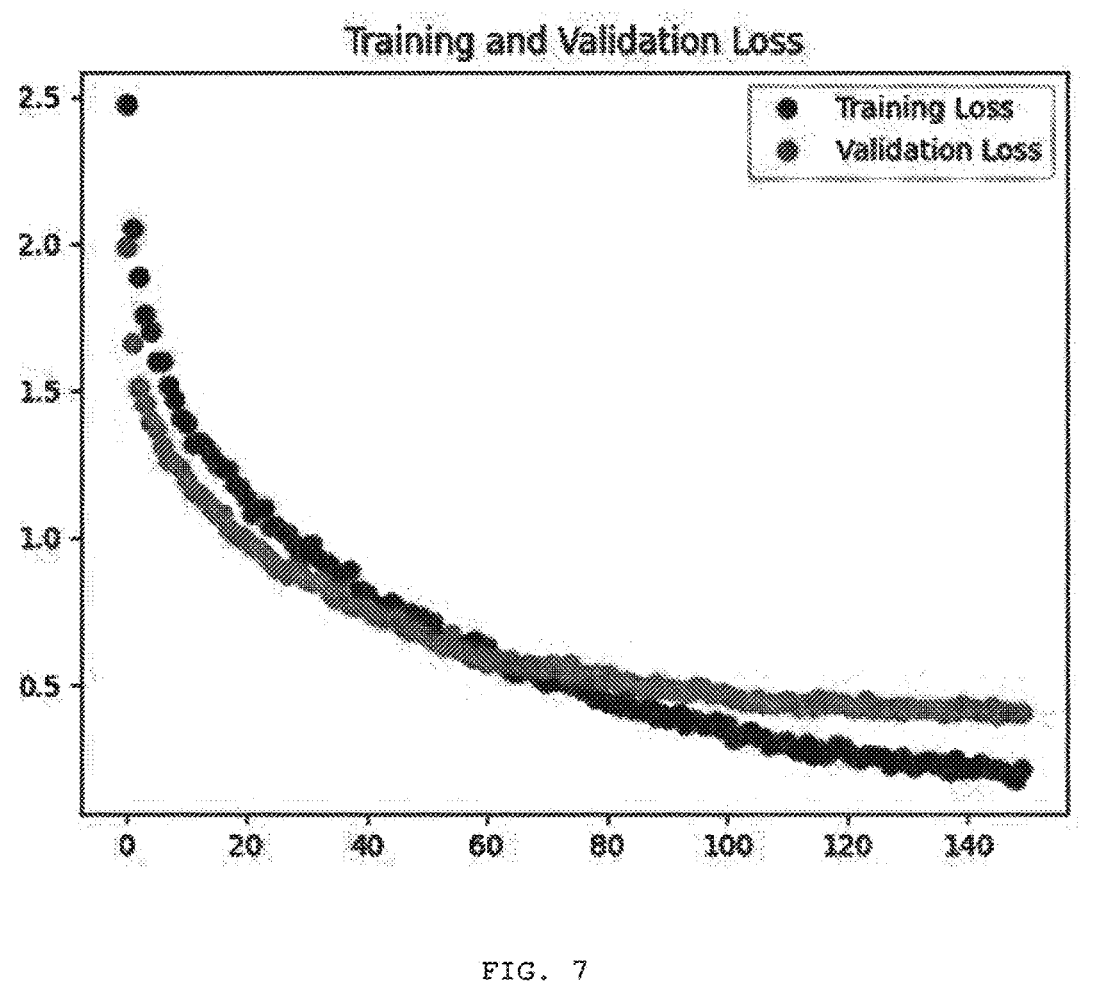

An embodiment of the classification network 100, as seen in FIG. 5, can classify according to bleeding potential as N: normal, POL: lymphangiectasia, PDX: Xanthelasma, P1E: erosion, P1PE: petechia, P1U e P2U: ulcers, P1PR and P2PR: bulge, P2V: vascular, P3: blood, are shown and grouped accordingly. At a given iteration of method 8000 (FIGS. 7, 8, and 9), the optimization pipeline described herein uses accuracy curves, ROC curves and AUC values and confusion matrix from training on a small subset of images and labelled data.

Figure 8:
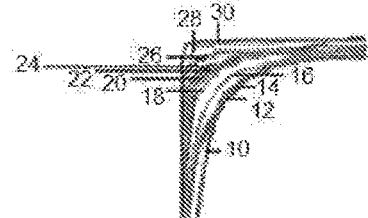
FIG. 8 illustrates exemplary ROC curves and AUC values obtained after training on a small subset of images and labelled data according to an embodiment of the present invention. Results used for model selection. Example of results from an iteration of method 8000, and a zoom of the ROC curves.
Figure 8:
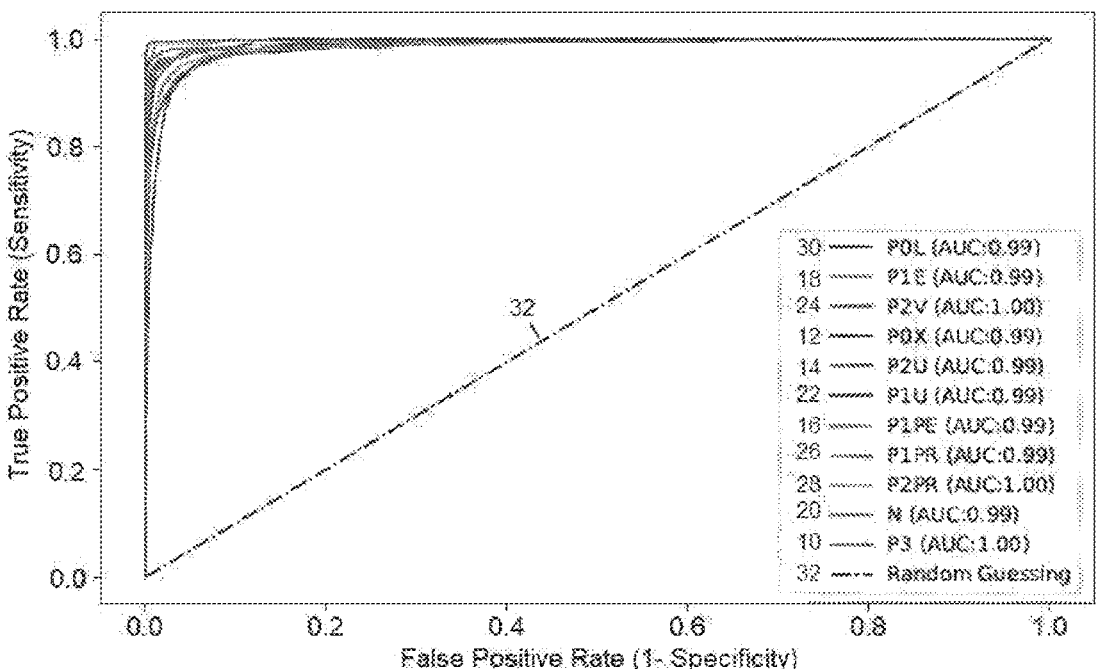

FIG. 8 illustrates exemplary ROC curves and AUC values obtained after training on a small subset of images and labelled data where 10 (P3-AUC: 1.00), 12 (PDX-AUC: 14 (P2U-AUC: 0.99), 16 (PIPE-AUC: 0.99), 18 (PIE-AUC: 0.99), 20 (N-AUC: 0.99), 22 (P1U-AUC: 0.99), 24 (P2V-AUC: 1.00), 26 (P1PR-AUC: 0.99), 28 (P2PR-AUC: 1.00), 30 (POL-AUC: 0.99) and 32 represent the Random Guessing.

Figure 9:
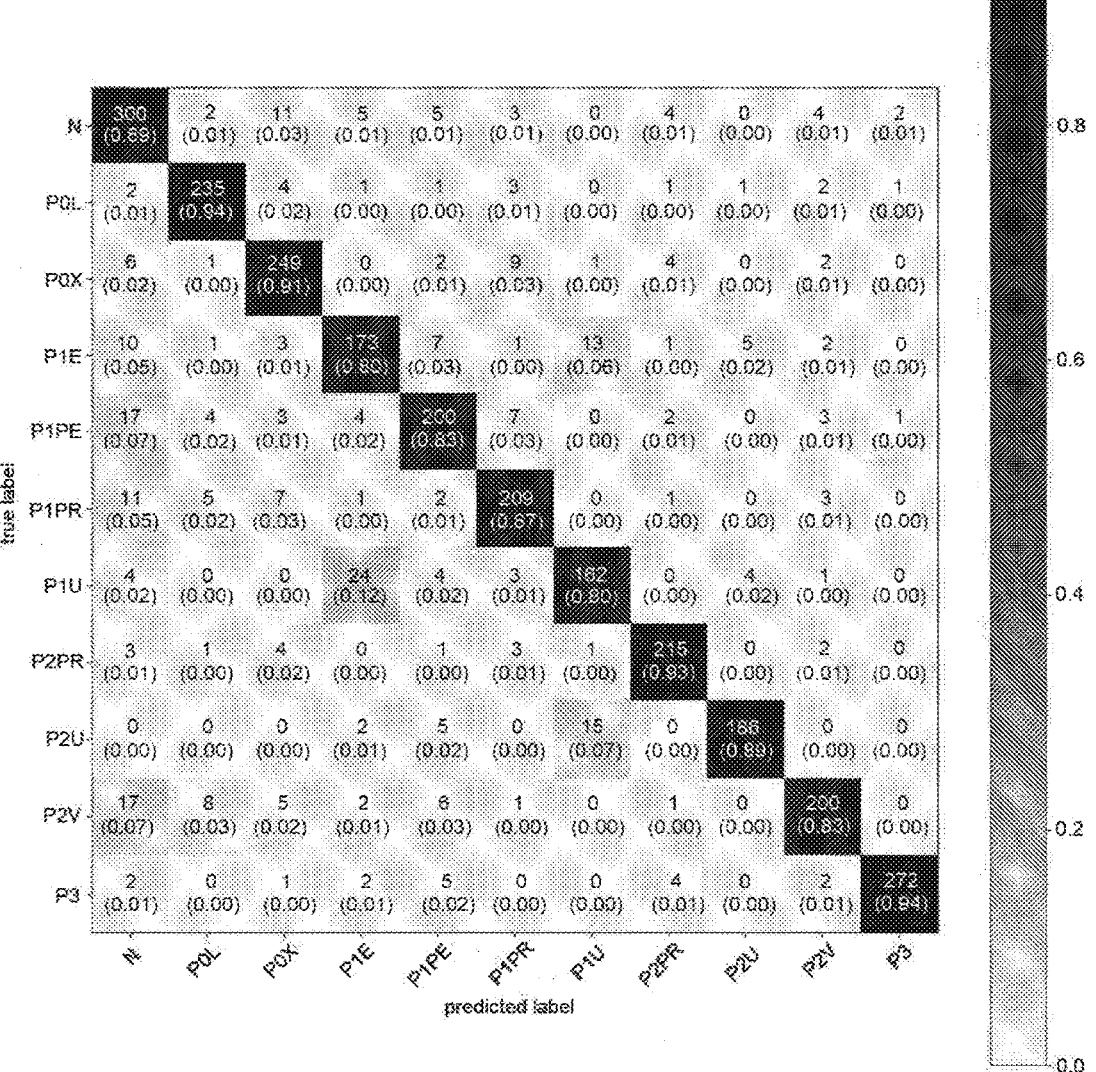
FIG. 9 illustrates an exemplary confusion matrix after training on a small subset of images and labelled data according to an embodiment of the present invention. Results used for model selection. Number of images of the small subset of data and respective class proportion between parentheses.

FIG. 9 illustrates an exemplary confusion matrix after training on a small subset of images and labelled data. Results used for model selection. Number of images of the small subset of data and respective class proportion between parentheses.

Figure 10:
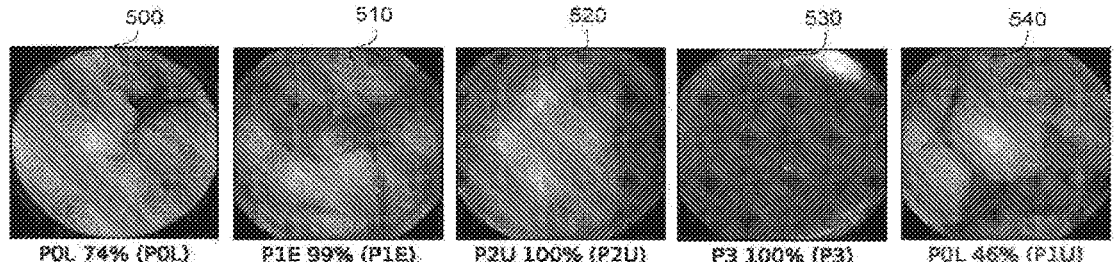
FIG. 10 illustrates examples of lesion classification according to an embodiment of the present invention.

FIG. 10 shows examples of lesion classification according to an embodiment of the present invention, where in 500 there is bleeding potential; lymphangiectasia, in 510 there is Low bleeding potential, in 520 there is High bleeding potential, ulcer, in 530 there is Blood and in 540 there is Low bleeding potential, ulcer.

FIG. 11 shows a result of performing deep learning-based lesion classification on the data volume 240 and 250, according to an embodiment of the present invention. The results of small bowel classification using the training method 8000 of the present invention are significantly improved as compared to the results using the existing methods (without method 8000).

Figure 12:
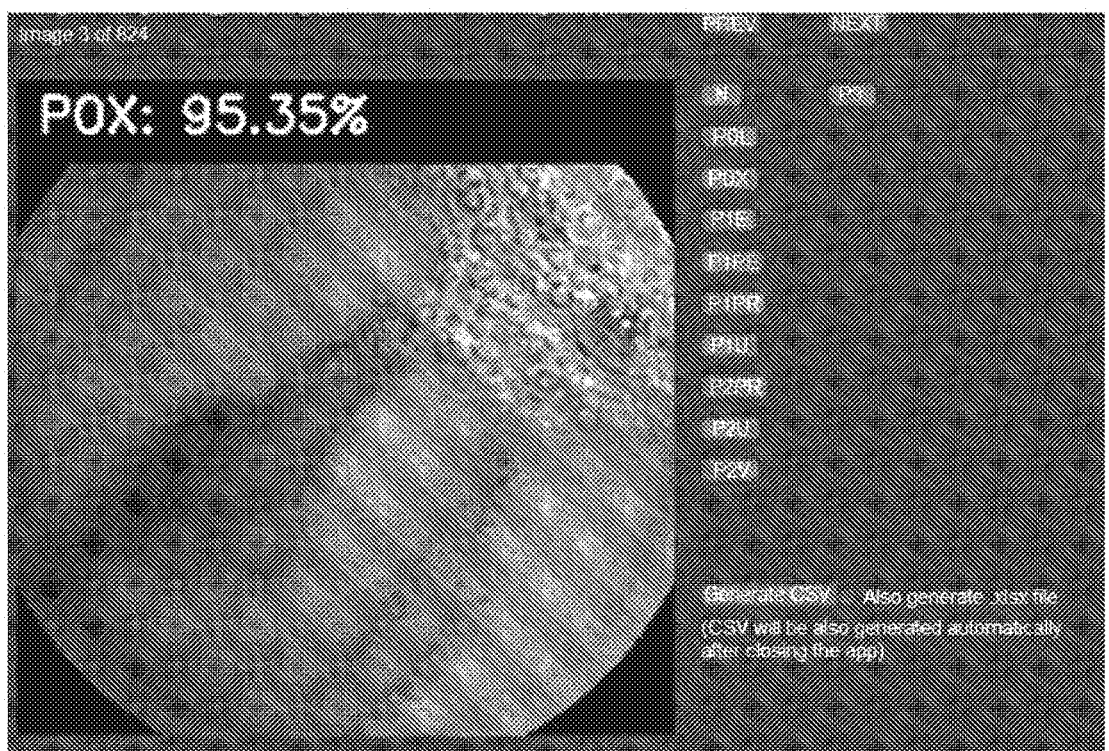
FIG. 12 illustrates an example of a classified lesion waiting for expert confirmation.

FIG. 12 shows an example of a classified lesion waiting for validation by the output collector module 7000. Merely as an example, a physician expert in gastroenterological imagery identifies small bowel lesions by analyzing the labelled image classified by the deep model 140.

Options for image reclassification on the last layer of the classification network 100 are depicted in FIG. 5. Optionally, confirmation or reclassification are sent to the storage module.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws.

It is to be understood that the embodiments shown and described herein are only illustrative of the principles of the present invention and that various modifications may be implemented by those skilled in the art within the scope of the appended claims.

The invention claimed is:

1. A computer-implemented method capable of automatically identifying and characterizing small bowel lesions in capsules colon colonoscopy medical images by classifying pixels as lesion or non-lesion, wherein such method comprises:

selecting a number of subsets of all colon capsule colonoscopy images, each of said subsets considering only images from a same patient;

selecting another subset as validation set, wherein the subset does not overlap chosen images on the previously selected subsets;

pre-training (8000) of each of chosen subsets with one of a plurality of combinations of convolutional neural network image feature extraction component, followed by a subsequent classification neural network component for pixel classification as small bowel lesion wherein said pre-training:

early stops when scores do not improved over a given number of epochs, namely three;

evaluates a performance of each of the combinations;

is repeated on new, different subsets, with another networks combination and training hyperparameters, wherein such new combination considers a higher number of dense layers if an f1 metric is low and fewer dense layers if f1 metric suggests overfitting;

selecting (400) an architecture combination that performs best during pre-training;

fully training and validating during training (9000) the selected architecture combination using an entire set of colon capsule colonoscopy images to obtain an optimized architecture combination;

prediction (6000) of small bowel lesions using said optimized architecture combination for classification;

receiving a classification output (270) of the prediction (6000) by an output collect module with means of communication to a third-party capable of performing validation by interpreting accuracy of the classification output and of correcting a wrong prediction, wherein the third-party comprises at least one of: another neural network, any other computational system adapted to perform the validation task or, optionally, a physician expert in gastroenterological imagery;

storing the corrected prediction into a storage component.

2. The method of claim 1, wherein the classification network architecture comprises at least two blocks, each having a Dense layer followed by a Dropout layer.

3. The method of claim 1 or 2, wherein the last block of the classification component includes a BatchNormalization layer followed by a Dense layer where the depth size is equal to the number of lesions type one desires to classify.

4. The method of claim 1, wherein the set of pre-trained neural networks is taken from a group including: VGG16, InceptionV3, Xception, EfficientNetB5, EfficientNetB7, Resnet50 and Resnet125.

5. The method of claim 1 or 4, wherein the best performing combination is chosen based on the overall accuracy and on the f1-metrics.

6. The method of claim 1 or 4, wherein the training of the best performing combination comprises two to four dense layers in sequence, starting with 40096 and decreasing in half up to 512.

7. The method of claim 1 or 4, wherein between the final two layers of the best performing combination there is a dropout layer of 0.1 drop rate.

8. The method of claim 1 or 4, wherein the training of the samples includes a ratio of training-to-validation of 10%-90%.

9. The method of claim 1 or 4, wherein the third-party validation is done by user-input.

10. The method of claim 1, wherein the training dataset includes images in the storage component that were predicted sequentially performing the steps of such method.

11. A portable endoscopic device comprising instructions which, when executed by a processor, cause the computer to carry out the steps of the method of claim 1, 2 or 4.

\* \* \* \* \*